United States Patent [19]
Ballard et al.

[11] Patent Number: 5,470,828
[45] Date of Patent: Nov. 28, 1995

[54] PEPTIDE ANALOGS OF INSULIN-LIKE GROWTH FACTOR II

[75] Inventors: Francis J. Ballard, Glenalta; John C. Wallace, Coromandel Valley; Julian R. E. Wells, College Park, all of Australia

[73] Assignee: Gropep Pty. Ltd., Australia

[21] Appl. No.: 947,514

[22] Filed: Sep. 17, 1992

Related U.S. Application Data

[63] Continuation-in-part of Ser. No. 408,518, Aug. 24, 1989, Pat. No. 5,164,370.

[30] Foreign Application Priority Data

Dec. 24, 1987 [AU] Australia .................................. PI 6068

[51] Int. Cl.$^6$ .................................................. A61K 38/30
[52] U.S. Cl. .............................. 514/12; 530/324; 530/399
[58] Field of Search .............................. 514/12; 530/324, 530/399

[56] References Cited

U.S. PATENT DOCUMENTS

| | | | |
|---|---|---|---|
| 4,876,242 | 10/1989 | Applebaum | 514/3 |
| 5,164,370 | 11/1992 | Ballard | 514/12 |

FOREIGN PATENT DOCUMENTS

| | | |
|---|---|---|
| 0158892 | 10/1985 | European Pat. Off. . |
| 0227619 | 7/1987 | European Pat. Off. . |
| 0309050 | 3/1989 | European Pat. Off. . |
| 0379338 | 7/1990 | European Pat. Off. . |
| WO85/00831 | 2/1985 | WIPO . |
| WO87/01038 | 2/1987 | WIPO . |

OTHER PUBLICATIONS

Francis, G. L., Aplin, S. E., Milner, S. J. McNeil, K. A. Ballard, F. J. & Wallace, J. C. "Insulin-like growth factor (IGF-II) binding to IGF-binding proteins and IGF receptors is modified by deletion of the N-terminal hexapeptide or substitution of Arg for Glu$^6$ in IGF-II: a comparison with the structurally equivalent analogues of IGF-I." Biochem. J. 293, 713-719 (1993).
Bagley et al., Biochem. J., 259, 665-671 (1989).
Bayne et al., Chemical Abstracts, 109, Abs. No. 17150r (1988).
Ballard et al., Biochem. and Biophys. Res. Commun., 149, 398-404 (1987).
Blumberg et al., Chemical Abstracts, 104, Abs. No. 203501c (1986).
Carlsson-Skwirut et al., Biochim. Biophys. Acta, 1011, 192-197 (1989).
Carlsson-Skwirut et al., Chemical Abstracts, 105, Abs. No. 36363w (1986).
Carlsson-Skwirut et al., Chemical Abstracts, 106, Abs. No. 96902b (1987).
Carlsson-Skwirut et al., FEBS, 201, 46-50 (1986).
Cascieri et al., Chemical Abstracts, 109, Abs. No. 86924h (1988).
Dawe et al., Chemical Abstracts, 108, Abs. No. 202006r (1988).
Fagerstedt et al., ACTA Endoctrinol, 103 (256), 216 (1983).
Francis et al., Chemical Abstracts, 108, Abs. No. 198502e (1988).
Merrifield, Angew. Chem. Int. Ed. Engl., 24, 799-810 (1985).
Nokihara et al., Chemical Abstracts, 97, Abs. No. 24215c (1982).
Rinderknecht et al., J. Biol. Chem., 253, 2769-2776 (1978).
Ross et al., Biochem J., 258, 267-272 (1989).
Rudinger, Peptide Hormones, (Parsons Ed.), University Park Press, 1-5 (1976).
Sara et al., Chemical Abstracts, 105, Abs. No. 73328j (1986).
Sara et al., Proc. Natl. Acad. Sci. USA, 78, 3175-3179 (1981).
Sara et al., Proc. Natl. Acad. Sci. USA, 83, 4904-4907 (1986).
Svoboda et al., Biochemistry, 19, 790-797 (1980).

Primary Examiner—Jill Warden
Assistant Examiner—David Lukton
Attorney, Agent, or Firm—Merchant, Gould, Smith, Edell, Welter & Schmidt

[57] ABSTRACT

The invention provides peptide analogues of insulin-like growth factor-1 (IGF-1) or factor-2 (IGF-2). The peptide analogues of IGF-1 have at least the glutamic acid residue at position 3 replaced by another amino acid. The peptide analogues of IGF-2 are replaced at position 5 or 6 with another amino acid.

3 Claims, No Drawings

PEPTIDE ANALOGS OF INSULIN-LIKE GROWTH FACTOR II

This application is a continuation-in-part application of U.S. application Ser. No. 07/408,518 filed Aug. 24, 1989 now U.S. Pat. No. 5,164,370 issued Nov. 17, 1992.

This invention relates to growth factors, related compounds and their use.

Insulin-like growth factor-1, a somatomedin, is a small protein that has been shown to stimulate growth of a wide range of cells in culture. Human IGF-1 (hIGF-1) has been purified to homogeneity from human serum and its complete amino acid sequence established. The serum mediator of growth hormone action, somatomedin C, has been shown to have an identical sequence to hIGF-1 so that these two are now considered as being synonymous. The amino acid sequence established for hIGF-1 beginning with the N-terminal glycine is:

Gly—pro—glu—thr—leu—cyc—gly—ala—glu—leu—
val—asp—ala—leu—gln—phe—val—cys—gly—asp—
arg—gly—phe—tyr—phe—asn—lys—pro—thr—gly—
tyr—gly—ser—ser—ser—arg—arg—ala—pro—gln—
thr—gly—ile—val—asp—glu—cys—cys—phe—arg—
ser—cys—asp—leu—arg—arg—leu—glu—met—tyr—
cys—ala—pro—leu—lys—pro—ala—lys—ser—ala—

Bovine IGF-1 and porcine IGF-1 have identical sequences.

Using the conventional numbering system of the N-terminal glycine being residue #1 and the C-terminal alanine residue #70, ovine and chicken IGF-1 differ from human IGF-1 only as follows:

ovine IGF-1:   ala$^{66}$
Chicken IGF-1: ser$^{26}$; leu$^{38}$; his$^{39}$; his$^{40}$;
               lys$^{41}$; gln$^{50}$; ile$^{64}$; pro$^{67}$ IGF-1 levels in serum correlate positively with growth rates in boys during adolescence and negatively with the degree of growth hormone deficiency in growth-retarded subjects, and to both growth rate and eventual size in mice transfected with growth hormone genes. These findings, indirectly linking IGF-1 concentrations with growth rates and supported by more direct evidence that administration of IGF-1 leads to restoration of growth rates in hypopituitary (growth hormone deficient) rats or mice and to increased growth rates in normal rats, have lead to the interpretation that IGF-1 might usefully be applied: (1) in humans to treat growth hormone deficiencies; (2) in farm animals to increase growth rates, increase the relative proportion of muscle and enhance food conversion efficiency. It is further suggested that administration of IGF-1; (3) may suppress the loss of body protein in severe human catabolic states such as following burns, infection or other trauma; (4) may improve wound healing in human subjects as well as in animals. IGF-1 can also be used to (5) support the growth of calls in culture.

The result of the above inferences is that there is a commercial demand for IGF-1 for use in animal trials, clinical investigations and for cell culture. However, only milligram amounts of hIGF-1, for example, are available by purification of tonnes of human serum protein and yields from recombinant DNA methods remain low.

Insulin-like growth factor-2 (IGF-2) like IGF-1, is a small protein that has been shown to stimulate growth of cells in culture. In most cases, these biological effects occur following interaction of IGF-2 with the same cellular receptor as is involved in IGF-1 actions. The amino acid sequence established for human IGF-2 (hIGF-2) beginning with the N-terminal alanine is shown below. Upper case letters have been used to indicate the amino acids equivalent to the N-terminal 5 amino acids of hIGF-1;

Ala—tyr—arg—PRO—SER—GLU—THR—LEU—cys—gly—
gly—glu—leu—val—asp—thr—leu—gln—phe—val—
cys—gly—asp—arg—gly—phe—tyr—phe—ser—arg—
pro—ala—ser—arg—val—ser—arg—arg—ser—arg—
gly—ile—val—glu—glu—cys—cys—phe—arg—ser—
cys—asp—leu—ala—leu—leu—glu—thr—tyr—cys—
ala—thr—pro—ala—lys—ser—glu Using the conventional numbering system of the N-terminal alanine being residue #1 and the C-terminal glutamic acid being residue #67, bovine, ovine, porcine and chicken IGF-2 differ from human IGF-2 only as follows:

bovine IGF-2:   ser$^{32}$; ile$^{35}$; asn$^{36}$
ovine IGF-2:    ser$^{32}$; ile$^{35}$; asn$^{36}$; ala$^{62}$
porcine IGF-2:  asn$^{36}$
chicken IGF-2:  ala$^1$ missing; gly$^3$; thr$^4$;
                ala$^5$; val$^{32}$; gly$^{33}$; asn$^{35}$;
                asn$^{36}$; ile$^{39}$; asn$^{40}$ It has been disclosed (see PCT/AU87/00246 to applicants) that compounds corresponding to IGF-1 but lacking one to five, preferably three amino acid residues from the N-terminal of the molecule can exhibit a substantial increase in biological potency compared with the more complete compounds.

For example, the compound destripeptide bIGF-1 but lacking the amino acid residues gly, pro and glu from the N-terminal, is effective in inhibiting protein breakdown and stimulating both protein synthesis and DNA synthesis in cellular systems at concentrations between 4 and 50 fold lower than required for entire bIGF-1.

For IGF-1 peptides having N-terminal amino acid sequences in common with that of human/bovine/porcine IGF-1, the elimination of between 1 and 5 amino acid residues from the N-terminal also results in enhanced biological potencies. The said N-terminal amino acid sequence is also a feature of the IGF-1 of rat, ovine, and chick species.

However, a useful property of the full IGF-1 peptide but not shared by the IGF-1 peptides having 1 to 5 N-terminal amino acids eliminated is that production by recombinant DNA methods that are part of the prior art are facilitated by the existence of N-terminal glycine. This facilitation occurs because an asparagine residue can be engineered upstream from the glycine and the asparagine/glycine bond cleaved selectively by mild hydroxylamine treatment following expression of the engineered gene.

Accordingly it is an object of the present invention to overcome, or at least alleviate, one or more of the difficulties related to the prior art.

Accordingly in a first aspect of the present invention there is provided a peptide analogue of insulin-like growth factor-1 (IGF-1) or factor-2 (IGF-2) where at least the glutamic acid residue is replaced at position 3 from the N-terminal of IGF-1 by amino acid residue selected from the group comprising:

| | |
|---|---|
| Alanine | (Ala) |
| Asparagine | (Asn) |
| Phenylalanine | (Phe) |

-continued

| | |
|---|---|
| Isoleucine | (Ile) |
| Methionine | (Met) |
| Valine | (Val) |
| Serine | (Ser) |
| Proline | (Pro) |
| Threonine | (Thr) |
| Tyrosine | (Tyr) |
| Cysteine | (Cys) |
| Tryptophan | (Trp) | or at position 5 or 6 from the N-terminal of IGF-2 by an amino acid reside selected from the group comprising:

| | |
|---|---|
| Alanine | (Ala) |
| Asparagine | (Asn) |
| Phenylalanine | (Phe) |
| Isoleucine | (Ile) |
| Methionine | (Met) |
| Valine | (Val) |
| Serine | (Ser) |
| Proline | (Pro) |
| Threonine | (Thr) |
| Tyrosine | (Tyr) |
| Cysteine | (Cys) |
| Tryptophan | (Trp) |
| Leucine | (Leu) | or is absent at position 5 or 6 from the N-terminal of IGF-2 and at least one of the $Ala^1$, $Tyr^2$, $Arg^3$, $Pro^4$ or $Ser^5$ residues is also absent.

It will be understood that in respect of chicken IGF-2 the N-terminal Ala-residue is absent so that the glutamic acid residue is at position 5 from the N-terminal.

Preferably the peptide analogue is a human, bovine, ovine, porcine or chicken insulin-like growth factor-1 or factor-2 analogue.

The peptide analogue according to the present invention may be in a biologically pure form.

The peptides lacking the glutamic acid residue or those having the glutamic acid replaced by any one of the following groups:

| | |
|---|---|
| Alanine | (Ala) |
| Asparagine | (Asn) |
| Phenylalanine | (Phe) |
| Isoleucine | (Ile) |
| Methionine | (Met) |
| Valine | (Val) |
| Serine | (Ser) |
| Proline | (Pro) |
| Threonine | (Thr) |
| Tyrosine | (Tyr) |
| Cysteine | (Cys) |
| Tryptophan | (Trp) |
| Leucine | (Leu) | bind poorly to the binding proteins produced by many cell types. Should a binding protein be present those other IGF-1 peptides that do bind have reduced potencies.

The peptide analogues according to the present invention may form suitable replacements for IGF-1 and -2 in the following applications: (1) in humans to treat growth hormone deficiencies; (2) in farm animals to increae growth rates, increase the relative proportion of muscle or improve food conversion efficiency; (3) in humans to suppress the loss of body protein in severe catabolic states such as following burns, infection or other trauma; (4) in humans and animals to improve wound healing, and (5) to support the growth of cells in culture:

More specifically, the present invention provides a pharmaceutical or veterinary composition that includes:

(a) an effective amount of a peptide analogue of insulin-like growth factor-1 (IGF-1) or factor-2 (IGF-2) wherein at least the glutamic acid residue is replaced at position 3 from the N-terminal of IGF-1 by an amino acid selected from the group comprising:

| | |
|---|---|
| Alanine | (Ala) |
| Asparagine | (Asn) |
| Phenylalanine | (Phe) |
| Isoleucine | (Ile) |
| Methionine | (Met) |
| Valine | (Val) |
| Serine | (Ser) |
| Proline | (Pro) |
| Threonine | (Thr) |
| Tyrosine | (Tyr) |
| Cysteine | (Cys) |
| Tryptophan | (Trp) | or at position 5 or 6 from the N-terminal of IGF-2 by an amino acid selected from the group comprising:

| | |
|---|---|
| Alanine | (Ala) |
| Asparagine | (Asn) |
| Phenylalanine | (Phe) |
| Isoleucine | (Ile) |
| Methionine | (Met) |
| Valine | (Val) |
| Serine | (Ser) |
| Proline | (Pro) |
| Threonine | (Thr) |
| Tyrosine | (Tyr) |
| Cysteine | (Cys) |
| Tryptophan | (Trp) |
| Leucine | (Leu) | or is absent at position 5 or 6 from the N-terminal of IGF-2 and at least one of the $Ala^1$, $Tyr^2$, $Arg^3$, $Pro^4$ or $Ser^5$ residues is also absent respectively and (b) a pharmaceutically or veterinarily acceptable diluent, carrier or excipient therefor.

The peptide analogue may be present in amounts sufficient to provide a dose rate of approximately 0.01 to 10, preferably 0.1 to 1 milligrams/kg body weight/day. The peptide analogue may be present in amounts of from approximately 0.02 to 2000 milligrams. For cell culture applications the peptide analogue may be present in concentrations from approximately 0.1 to 100 milligrams per litre.

In a further preferred aspect of the present invention there is provided a method for the treatment of protein accumulation deficiencies or protein loss in human subjects, which method includes administering to a patient to be treated an effective amount of a peptide analogue of insulin-like growth factor-1 (IGF-1) or factor-2 (IGF-2) as described above.

The peptide analogues may be administered to human subjects as a treatment for disorders associated with tissue wasting including, but not limited to, burns, skeletal trauma, infection, cancer, cystic fibrosis, Duchenne muscular dystrophy, Becker dystrophy, autosomal recessive dystrophy, polymyositis as well as other myopathies and acquired immune deficiency syndrome (AIDS). The peptide analogues may be administered parenterally or by injection.

In an alternative aspect there is provided a method for the treatment of wounds in animals including humans, which method includes administering to a patient to be treated an effective amount of a peptide analogue of mammalian insulin-like growth factor-1 (IGF-1) or factor-2 (IGF-2) as described above For the treatment of wounds in human subjects or in animals the peptide analogue may be applied externally to the wound or it may be administered by injection.

In a still further aspect there is provided a method for the improvement of growth performance in animals which method includes administering to an animal to be treated an effective amount of a peptide analogue of insulin-like growth factor-1 (IGF-1) or factor-2 (IGF-2) as described above.

An implant, preferably a slow release pellet, is the preferred method of administration to farm animals as applied in conventional practice. Otherwise the peptide analogue may be administered by injection.

The peptide analogues of the present invention may be administered to premature or other human infants to promote growth, improve nitrogen status and to treat catabolic disorders. The peptides may be administered as outline above for tissue wasting conditions.

Accordingly in a still further aspect of the present invention, there is provided a method for the stimulation of cells in culture which method includes providing a culture medium, and an effective amount of a peptide analogue as described above; and adding the peptide analogue to the culture medium.

Any standard culture medium may be used in accordance with this aspect of the present invention. For example the culture medium may include Eagle's Minimal Essential Medium.

A preferred method for the preparation of a peptide analogue of IGF-1 wherein at least the glutamic acid residue is substituted at position 3 from the N-terminal includes providing a source of amino acids, and coupling the amino acids in sequence to form a peptide analogue.

The peptide analogues may be produced by appropriate modifications to methods existing for the production of the full IGF-1 peptide. These modifications would be familiar to those familiar with the art.

Specifically, the peptides related to human/bovine/porcine IGF-1 may be synthesized chemically using procedures developed for human IGF-1 (for example: Li et al., Proc. Natl. Acad. Sci, USA 80: 2216–2220, 1983) but with the final cycles of amino acid ligation modified. Synthetic ovine or chicken IGF-1 as well as related IGF-1 and IGF-2 peptides may be produced by techniques similar to those used for human IGF-1 using amino acid sequence information for these peptides.

The peptides may also be produced following transformation of susceptible bacterial, yeast or tissue culture cell hosts with recombinant plasmids that include DNA sequences capable of directing the expression of the peptides. The DNA sequence may be synthetic, chromosomal, cDNA or combination thereof. The inserted coding sequences may incorporate deletion or omissions to account for differences between the sequence of peptide analogues and the full IGF-1 peptide.

An example to illustrate one method of synthesis of these compounds will now be provided. It should be understood however, that the following description is illustrative only and should not be taken in any way as a restriction on the generality of the description foregoing.

EXAMPLE 1

Synthesis of IGF-1 peptides

Chemical synthesis of human/bovine/porcine IGF-1 peptides with between 1 and 4 amino acids from the normal N-terminal modified may be effected by the following procedure.

The starting material may be Boc-ala-phenylacetamido methyl resin. Coupling may be effected in an Applied Biosystems Inc model 430A peptide synthesiser with preformed symmetric anhydrides of the Bos-aminoacids in dichloromethane except for the derivatives of arginine, asparagine and glutamine which can be coupled in dimethyl formamide (DMF). In all cases a second coupling may be performed in DMF. Samples of resin can be removed after each cycle of synthesis and subjected to quantitive ninhydrin analysis (Sarin, V. K., Kent, S. B. H., Tam, J. P., Merifield, R. B.; Anal. Biochem. 17, 147–157 (1981)). Preview sequence analysis of the side-chain protected, resin-bound peptide may also be carried out.

Portions of resin containing side-chain protected peptides corresponding to the complete sequence of hIGF-1 but with 4 to 0 amino acids not coupled at the N-terminal will be removed. Other portions with between 4 and 3 amino acids not coupled at the N-terminal may have amino acid residues coupled as required for specific analogues. Peptides will be cleaved and deprotected according to Applied Biosystems Inc procedures and recovered as ether precipitates.

Peptides may be redissolved in 6M guanidine hydrochloride pH 8.5 with Tris containing 10 mM dithioerythritol and desalted by reverse phase HPLC and dried. Oxidation of the reduced peptide will be effected by dissolving in 8M urea, 0.1M Tris (pH 8.0 with HCl) containing 13 mM oxidized gluthathione and incubated at 25° for 15 hours. The sample can be purified by reverse phase HPLC using a gradient of acetonitrile in 0.1% trifluoroacetic acid to elute the peptides and separate the biologically active form of the peptide from those forms lacking the correct disulphide bonds and hence lacking full biological activity. The samples can be dried prior to resuspension.

Biological activity may be confirmed by the ability of the peptide to stimulate protein synthesis in L6 myoblasts.

It will be appreciated that various modifications and/or alterations may be introduced into the constructions and arrangements of parts previously described without departing from the spirit or ambit of the present invention.

We claim:

1. A peptide analog of human bovine, ovine, porcine or chicken insulin-like growth factor II (IGF-II) having the following modified N-terminal sequence:

Thr-Leu-Cyswith the Cys residue shown being the amino acid residue at position 8 or 9 from the N-terminal of the native amino acid sequence of the IGF-II with the remainder of the IGF-II peptide analog sequence being an amino acid sequence of a human, bovine, ovine, porcine or chicken IGF-II beginning at the amino acid residue immediately following the Cys residue at position 8 or 9 from the N-terminal of the native IGF-II amino acid sequence.

2. A pharmaceutical composition for the treatment of protein accumulation deficiencies or protein loss in humans wherein said composition comprises an effective amount of a peptide analog according to claim 1.

3. A veterinary composition for the treatment of protein accumulation deficiencies or protein loss in animals wherein said composition comprises an effective amount of a peptide analog according to claim 1.

* * * * *

UNITED STATES PATENT AND TRADEMARK OFFICE
CERTIFICATE OF CORRECTION

PATENT NO. : 5,470,828

DATED : November 28, 1995

INVENTOR(S) : Ballard et al.

It is certified that error appears in the above-indentified patent and that said Letters Patent is hereby corrected as shown below:

ON THE TITLE PAGE:

Please insert "[63] PCT No.:PCT/AU88/00485 Aug. 24, 1989

Col. 1, line 20 "cyc" should read --cys--

Col. 1, line 56 "calls" should read --cells--

Col. 2, line 43 "chick" should read --chicken--

Col. 2, line 60 insert --an-- after the word --by--

Signed and Sealed this

Thirtieth Day of September, 1997

Attest:

BRUCE LEHMAN

Attesting Officer     Commissioner of Patents and Trademarks